(12) United States Patent
Stoeber et al.

(10) Patent No.: US 9,675,790 B2
(45) Date of Patent: Jun. 13, 2017

(54) METALLIC MICRONEEDLES

(71) Applicant: MICRODERMICS INC., Vancouver (CA)

(72) Inventors: Boris Stoeber, Vancouver (CA); Iman Mansoor, West Vancouver (CA); Urs Otto Häfeli, Vancouver (CA)

(73) Assignee: Microdermics Inc., Vancouver, BC (CA)

( * ) Notice: Subject to any disclaimer, the term of this patent is extended or adjusted under 35 U.S.C. 154(b) by 0 days.

(21) Appl. No.: 14/965,536

(22) Filed: Dec. 10, 2015

(65) Prior Publication Data

US 2016/0158514 A1    Jun. 9, 2016

Related U.S. Application Data

(63) Continuation of application No. PCT/CA2014/050552, filed on Jun. 12, 2014.
(Continued)

(51) Int. Cl.
*A61M 37/00* (2006.01)
*B05D 1/36* (2006.01)
(Continued)

(52) U.S. Cl.
CPC .......... *A61M 37/0015* (2013.01); *B05D 1/36* (2013.01); *B21G 1/00* (2013.01); *B81C 1/00111* (2013.01); *A61M 2037/003* (2013.01); *A61M 2037/0023* (2013.01); *A61M 2037/0053* (2013.01); *B05D 2201/06* (2013.01)

(58) Field of Classification Search
CPC ............................................. A61M 2037/0053
See application file for complete search history.

(56) References Cited

U.S. PATENT DOCUMENTS

| 4,908,213 A | 3/1990 | Govil et al. |
| 5,262,165 A | 11/1993 | Govil et al. |

(Continued)

FOREIGN PATENT DOCUMENTS

| DE | 4241045 C1 | 5/1994 |
| WO | 2004035054 A1 | 4/2004 |

(Continued)

OTHER PUBLICATIONS

P. Griss, P. Enoksson, and G. Stemme, "Micromachined barbed spikes for mechanical chip attachment", Sensors and Actuators A, vol. 95, pp. 94-99, 2002.
(Continued)

*Primary Examiner* — Cachet Sellman
(74) *Attorney, Agent, or Firm* — Todd A. Rattray; Oyen Wiggs Green & Mutala LLP

(57) ABSTRACT

Methods for fabricating metallic microneedles are disclosed. One method comprises providing a mold pillar; forming an apertured electrically-conductive layer over the mold pillar; and depositing a metal layer over the electrically-conductive layer to provide an apertured microneedle. Another method comprises providing a mold pillar; depositing a first metal layer over the mold pillar to provide a first microneedle; removing the first microneedle from the mold pillar; and depositing a second metal layer over the mold pillar to provide a second microneedle.

22 Claims, 5 Drawing Sheets

Related U.S. Application Data

(60) Provisional application No. 61/834,482, filed on Jun. 13, 2013.

(51) Int. Cl.
*B29C 33/60* (2006.01)
*B21G 1/00* (2006.01)
*B81C 1/00* (2006.01)

(56) References Cited

U.S. PATENT DOCUMENTS

| | | | |
|---|---|---|---|
| 6,334,856 B1* | 1/2002 | Allen | A61B 5/14514 128/898 |
| 6,451,240 B1* | 9/2002 | Sherman | B26F 1/24 205/164 |
| 6,503,231 B1 | 1/2003 | Prausnitz et al. | |
| 6,565,532 B1 | 5/2003 | Yuzhakov et al. | |
| 7,556,823 B2 | 7/2009 | Miller et al. | |
| 7,627,938 B2 | 12/2009 | Kim et al. | |
| 8,048,017 B2 | 11/2011 | Xu | |
| 8,402,629 B2* | 3/2013 | Lee | A61B 5/685 29/458 |
| 2002/0138049 A1* | 9/2002 | Allen | A61B 5/14514 604/272 |
| 2002/0190426 A1* | 12/2002 | Seidner | C08L 83/04 264/219 |
| 2006/0015061 A1* | 1/2006 | Kuo | A61B 17/205 604/47 |
| 2006/0025717 A1 | 2/2006 | Zimmerman et al. | |
| 2006/0084942 A1* | 4/2006 | Kim | A61K 9/0021 604/890.1 |
| 2008/0063866 A1 | 3/2008 | Allen et al. | |
| 2008/0097352 A1 | 4/2008 | Beck et al. | |
| 2009/0093775 A1* | 4/2009 | Raju | A61M 37/0015 604/272 |
| 2010/0062142 A1* | 3/2010 | Zhu | A61M 37/0015 427/2.3 |
| 2011/0005669 A1 | 1/2011 | Lee et al. | |
| 2013/0116523 A1 | 5/2013 | Jung et al. | |

FOREIGN PATENT DOCUMENTS

| | | |
|---|---|---|
| WO | 2009072830 A2 | 6/2009 |
| WO | 2014197995 A1 | 12/2014 |

OTHER PUBLICATIONS

J.-H. Park, S. Davis, Y.-K. Yoon, M.R. Prausnitz, and M.G. Allen, "Micromachined Biodegradable Microstructures", Proceedings of 16th Annual International Conference on Micro Electro Mechanical Systems, Kyoto, Japan, Jan. 19-Jan. 23, 2003, pp. 371-374, 2003.
M. Shikida, M. Odagaki, N. Todoroki, M. Ando, Y. Ishihara, T. Ando, and K. Sato, "Non-Photolithographic Pattern Transfer for Fabricating Arrayed 3-D Microstructures by Chemical Anisotropic Etching", Proceedings of 16th Annual International Conference on Micro Electro Mechanical Systems, Kyoto, Japan, Jan. 19-Jan. 23, 2003, pp. 562-565, 2003.
A. Trautmann, P. Ruther, and O. Paul, "Microneedle Arrays Fabricated Using Suspended Etch Mask Technology Combined with Fluidic Through Wafer Vias", Proceedings of 16th Annual International Conference on Micro Electro Mechanical Systems, Kyoto, Japan, Jan. 19-Jan. 23, 2003, pp. 682-685, 2003.
F. Chabri, K. Bouris, T. Jones, D. Barrow, A. Hann, C. Allender, K. Brain, and J. Birchall, "Microfabricated silicon microneedles for nonviral cutaneous gene delivery", British Journal of Dermatology, vol. 150, pp. 869-877, 2004.
L. Lin, and A.P. Pisano, "Silicon-Processed Microneedles", Journal of Microelectromechanical Systems, vol. 8, No. 1, pp. 78-84, 1999.
K.S. Lebouitz, and A.P. Pisano, "Microneedles and microlancets fabricated using SOI wafers and isotropic etching", Proceedings Microstructures and Microfabrication Systems IV, Boston, MA, U.S.A., 1998, pp. 235-244, 1998.
J. Chen, K.D. Wise, J.F. Hetke, and S.C. Bledsoe, Jr., "A Multichannel Neural Probe for Selective Chemical Delivery at the Cellular Level", IEEE Transactions on Biomedical Engineering, vol. 44, No. 8, pp. 760-769, 1997.
J. Brazzle, I. Papautsky, and A.B. Frazier, "Micromachined Needle Arrays for Drug Delivery or Fluid Extraction",IEEE Engineering in Medicine and Biology Magazine, vol. 18, No. 6, pp. 53-58, 1999.
S. Chandrasekaran, J. Brazzle, and A.B. Frazier, "Surface Micromachined Metallic Microneedles", Journal of Microelectromechanical Systems, vol. 12, No. 3, pp. 281-288, 2003.
P.A. Stupar, and A.P. Pisano, "Silicon, Parylene, and Silicon/Parylene Micro-Needles for Strength and Toughness", Digest of Technical papers of the 11th International Conference on Solid-State Sensors and Actuators—Tranducers '01, Eurosensors XV, Jun. 10-14, 2001 Munich, Germany, pp. 1386-1389, 2001.
B. Stoeber, and D. Liepmann, "Fluid injection through out-of-plane microneedles", Proceedings of the 1st Annual International IEEE-EMBS Special Topic Conference on Microtechnologies in Medicine and Biology, Lyon, France Oct. 12-Oct. 14, 2000, pp. 224-228, 2000.
Cheng Guo Li, Cheng Yeol Lee, Kwang Lee, and Hyungil Jung, "An optimized hollow microneedle for minimally invasive blood extraction", Biomed Microdevices, vol. 15, No. 1, pp. 17-25, 2012.
Kabseong Kim and Jeong-Bong Lee, "High aspect ratio tapered hollow metallic microneedle arrays with microfluidic interconnector", Microsystem Technologies, vol. 13, No. 3-4, pp. 231-235, 2007.
Ryan F. Donnelly, Thakur Raghu Raj Singh, and A. David Woolfson, "Microneedle-based drug delivery systems: Microfabrication, drug delivery, and safety", Drug Delivery, vol. 17(4), pp. 187-207, 2010.
P. Griss, P. Enoksson, H.K. Tolvanen-Laakso, P. Meriläinen, S. Ollmar, and G. Stemme, "Micromachined Electrodes for Biopotential Measurements", Journal of Microelectromechanical Systems, vol. 10, No. 1, pp. 10-16, 2001.
Iman Mansoor, Urs O. Häfeli, and Boris Stoeber, "Hollow Out-of-Plane Polymer Microneedles Made by Solvent Casting for Transdermal Drug Delivery"—Journal of Microelectromechanical Systems, vol. 21, No. 1., Feb. 2012.
I. Mansoor, Y. Liu, U.O. Häfeli, and Boris Stoeber, Fabrication of Hollow Microneedle Arrays Using Electrodeposition of Metal onto Solvent Cast Conductive Polymer Structures. Transducers 2013, Barcelona, Spain, Jun. 16-20, 2013. pp. 373-376.
D. V. McAllister et al., Microfabricated needles for transdermal delivery of macromolecules and nanoparticles: Fabrication methods and transport studies, (2003), Proc. Nat. Acad. Sci. USA, vol. 100(24), pp. 13755-13760.
B. Stoeber, D. Liepmann, Arrays of Hollow out-of-Plane Microneedles for Drug Delivery, (2005), J. Microelectromech. Syst., vol. 14, No. 3, pp. 472-479.
S. P. Davis et al., Hollow metal microneedles for insulin delivery to diabetic rats, (2005), IEEE Trans. Biomed. Eng., vol. 52, pp. 909-915, No. 5.
Boris Stoeber, Microneedles for Biomedical Applications, MolES/Nanotechnology Seminar Series, University of Washington, Oct. 1, 2013.
Iman Mansoor, Fabrication of out-of-plane microneedles for drug delivery and biosensing, https://open.library.ubc.ca/clRcle/collections/ubctheses/24/items/1.0103392, Nov. 30, 2011.
M. R. Prausnitz and R. Langer, "Transdermal drug delivery," Nature Biotechnology, vol. 26, No. 11, pp. 1261-1268, 2008.
S. Venkatraman and R. Gale, "Skin adhesives and skin adhesion: 1. Transdermal drug delivery systems," Biomaterials, vol. 19, pp. 1119-1136, 1998.
R. K. Sivamani, B. Stoeber, G. C. Wu, H. Zhai, D. Liepmann, H. Maibach, "Clinical Microneedle Injection of Methyl Nicotinate: Stratum Corneum Penetration", Skin Res. Technol., vol. 11, No. 2, pp. 152-156, 2005.

(56) References Cited

OTHER PUBLICATIONS

S. Kaushik, A. H. Hord D. D. Denson, D. V. McAllister, S. Smitra, M. G. Allen, and M. R. Prausnitz, "Lack of Pain Associated with Microfabricated Microneedles," Anesthesia & Analgesia, vol. 92, No. 2, pp. 502-504, 2001.
H. S. Gill, D. D. Denson, B. A. Burris, and M. R. Prausnitz, "Effect of Microneedle Design on Pain in Human Volunteers," The Clinical Journal of Pain, vol. 24, No. 7, pp. 585-594, 2008.
S. J. Paik, S. Byun, J. M. Lim, Y. Park, A. Lee, S. Chung, J. Chang, K. Chun, and D. Cho, "In-plane single-crystal-silicon microneedles for minimally invasive microfluid systems," Sensors and Actuators A: Physical, vol. 114, pp. 276-284, 2004.
S. Henry, D. V. Mcallister, M. G. Allen, and M. R. Prausnitz, "Microfabricated microneedles: A novel approach to transdermal drug delivery," Journal of Pharmaceutical Sciences, vol. 87, No. 8, pp. 922-925, 1998.
W. Martanto, S. Davis, N. Holiday, J. Wang, H. Gill, and M. Prausnitz, "Transdermal delivery of insulin using microneedles in vivo," Pharmaceutical Research, vol. 21, No. 6, pp. 947-952, 2004.
J.A. Mikszta, J.B. Alarcon, J.M. Brittingham, D.E. Sutter, R.J. Pettis, and N.G. Harvey, "Improved genetic immunization via micromechanical disruption of skinbarrier function and targeted epidermal delivery," Nature Medicine, vol. 8, No. 4, pp. 415-419, 2002.
H. J. G. E. Gardeniers, R. Luttge, E. J. W. Berenschot, M. J. de Boer, S. Y. Yeshurun, M. Hefetz, R.van't Oever, and A. van den Berg, "Silicon micromachined hollow microneedles for transdermal liquid transport," Journal of MEMS, vol. 12, No. 6, pp. 855-862, 2003.
J. Brazzle, D. Bartholomeusz, R. Davies, and J. Andrade, "Active microneedles with integrated functionality," Proceeding of Solid State Sensors and Actuators Workshop, Hilton Head, pp. 199-202, 2000.
J. Ji, F. E.H. Tay, and J. Miao, "Microfabricated Hollow Microneedle Array Using ICP Etcher," Journal of Physics: Conference Series, vol. 34, No. 34, pp. 1132-1136, 2006.
P. Griss and G. Stemme, "Side-opened out-of-plane microneedles for microfluidic transdermal liquid transfer," Journal of MEMS, vol. 12, No. 3, pp. 296-301, 2003.
E.V. Mukerjee, S.D. Collins, R.R. Isseroff, and R.L. Smith, "Microneedle array for transdermal biological fluid extraction and in situ analysis," Sensors and Actuators A, vol. 114, No. 2/3, pp. 267-275, 2004.
M. Shikida, M. Ando, Y. Ishihara, T. Ando, K. Sato, and K. Asaumi, "Nonphotolithographic pattern transfer for fabricating pen-shaped microneedle structures," Journal of Micromechanics and Microengineering, vol. 14, No. 11, pp. 1462-1467, 2004.
J. D. Zahn, N. H. Talbot, D. Liepmann, and A. P. Pisano, "Microfabricated Polysilicon Microneedles for Minimally Invasive Biomedical Devices," Biomedical Microdevices, vol. 2, No. 4, pp. 295-303, 2000.
K. Chun, G. Hashiguchi, H. Toshiyoshi, and H. Fujita, "Fabrication of array of hollow microcapillaries used for injection of genetic materials into animal/plant cells," Japanese Journal of Applied Physics, vol. 38, No. 38A, pp. L279-L281, 1999.
K. Kim, D. S. Park, H. M. Lu,W. Che, K. Kim, J. Lee, and C. H. Ahn, "A tapered hollow metallic microneedle array using backside exposure of SU-8," Journal of Micromechanics and Microengineering, vol. 14, No. 4, pp. 597-603, 2004.
J.A. Matriano, M. Cormier, J. Johnson, W.A. Young, M. Buttery, K. Nyam, and P.E. Daddona, "Macroflux microprojection array patch technology: a new and efficient approach for intracutaneous immunization," Pharmaceutical Research, vol. 19, No. 1, pp. 63-70, 2002.
S. Chandrasekaran and A. B. Frazier, "Characterization of Surface Micromachined Metallic Microneedles," Journal of Microelectromechanical Systems, vol. 12, No. 3, pp. 289-295, 2003.
J. D. Brazzle, I. Papautsky, and A. B. Frazier, "Hollow Metallic Micromachined Needle Arrays," Biomedical Microdevices, vol. 2, No. 3, pp. 197-205, 2000.
K. Kobayashi and H. Sizuki, "A sampling mechanism employing the phase transition of a gel and its application to a micro analysis system imitating a mosquito," Sensors and Actuators B, Chemical, vol. 80, No. 1, pp. 1-8, 2001.
S. J. Moon, S. S. Lee, H. S. Lee, and T. H. Kwon, "Fabrication of microneedle array using LIGA and hot embossing process," Microsystem Technologies, vol. 11, No. 4/5, pp. 311-318, 2005.
J. Park, M. G. Allen, M. R. Prausnitz, "Biodegradable polymer microneedles: Fabrication, mechanics and transdermal drug delivery," Journal of Controlled Release, vol. 104, No. 1, pp. 51-66, 2005.
M. Han, D. Hyun, H. Park, S. S Leel, C. Kim, and C. Kim, "A novel fabrication process for out-of-plane microneedle sheets of biocompatible polymer," Journal of Micromechanics and Microengineering, vol. 17, No. 6, pp. 1184-1191, 2007.
H. Huang and C. Fu, "Different fabrication methods of out-of-plane polymer hollow needle arrays and their variations," Journal of Micromechanics and Microengineering, vol. 17, No. 2, pp. 393-402, 2007.
S. Kuo and Y. Chou, "A Novel Polymer Microneedle Arrays and PDMS Micromolding Technique," Tamkang Journal of Science and Engineering, vol. 7, No. 2, pp. 95-98, 2004.
I. Mansoor, U.O. Häfeli, B. Stoeber, "Arrays of Solvent Cast Hollow Out-of-plane Polymer Microneedles for Drug Delivery", Proceedings of 2011 IEEE 24th International Conference on MEMS, pp. 1027-1030, 2011.
A. W. McFarland, M. A. Poggi, L. A. Bottomley, J. S. Colton, "Production and Characterization of Polymer Microcantilevers", Rev. Sci. Instrum., vol. 75(8), pp. 2756-2758, 2004.
Jeong W. Lee, Jung-Hwan Park, Mark R. Prausnitz, "Dissolving microneedles for transdermal drug delivery", Biomaterials, vol. 29(13), pp. 2113-2124, 2008.
S. P. Davis, B. J. Landis, Z. H. Adams, M. G. Allen, M. R. Prausnitz, "Insertion of Microneedles Into Skin: Measurement and Prediction of Insertion Force and Needle Fracture Force", J. Biomech., vol. 37(8), pp. 1155-1163, 2004.
S. Zimmermann, D. Fienbork, B. Stoeber, A.W. Flounders, and D. Liepmann, "A Microneedle-Based Glucose Monitor: Fabricated on a Wafer-Level Using In-Device Enzyme Immobilization", Technical Digest of the 12th International Conference on Solid-State Sensors, Actuators and Microsystems—Transducers '03, Boston, Massachusetts, U.S.A., Jun. 8-12, 2003, vol. 2, pp. 99-102, 2003.
K.D. Wise, J.B. Angell, and A. Starr, "An Integrated-Circuit Approach to Extracellular Microelectrodes", IEEE Transactions on Bio-Medical Engineering, vol. BME-17, No. 3, pp. 238-247, 1970. 197.
Q. Bai, and K.D. Wise, "Single-Unit Neural Recording with Active Microelectrode Arrays", IEEE Transactions on Biomedical Engineering, vol. 48, No. 8, pp. 911-920, 2001.
P.K. Campbell, K.E. Jones, R.J. Huber, K.W. Horch, and R.A. Normann, "A Silicon-Based, Three-Dimensional Neural Interface: Manufacturing Process for an Intracortical Electrode Array", IEEE Transactions on Biomedical Engineering, vol. 38, No. 8, pp. 758-768, Aug. 1991.

\* cited by examiner

METALLIC MICRONEEDLES

RELATED APPLICATIONS

This application is a continuation of PCT application No. PCT/CA2014/050552 having an international filing date of 12 Jun. 2014 which in turn claims the benefit of the priority of U.S. application No. 61/834,482 filed 13 Jun. 2013. Both of PCT application No. PCT/CA2014/050552 and U.S. application No. 61/834,482 are hereby incorporated herein by reference.

TECHNICAL FIELD

This invention relates to methods for fabricating mechanical microstructures. In particular, this invention relates to methods for fabricating metallic microneedles.

BACKGROUND

Various methods for fabricating microneedles are known. Examples of known techniques include those described in the following disclosures:
- D. V. McAllister et al., *Microfabricated needles for transdermal delivery of macromolecules and nanoparticles: Fabrication methods and transport studies*, (2003), Proc. Nat. Acad. Sci. USA, Vol. 100(24), pp. 13755-13760.
- B. Stoeber, D. Liepmann, *Arrays of Hollow out-of-Plane Microneedles for Drug Delivery*, (2005), J. Microelectromech. Syst., Vol. 14, no. 3, pp. 472-479.
- I. Mansoor et al. *Hollow Out-of-Plane Polymer Microneedles Made by Solvent Casting for Transdermal Drug Delivery*, (2012), J. Microelectromech. Syst., Vol. 21, pp. 44-52.
- S. P. Davis et al., *Hollow metal microneedles for insulin delivery to diabetic rats*, (2005), IEEE Trans. Biomed. Eng., Vol. 52, pp. 909-915.
- U.S. Pat. No. 7,627,938 (Kim et al.).

SUMMARY

The following embodiments and aspects thereof are described and illustrated in conjunction with methods and apparatus which are meant to be exemplary and illustrative, not limiting in scope.

One aspect of this invention provides a method for fabricating an apertured microneedle. The method comprises providing a mold pillar; forming an apertured electrically-conductive layer over the mold pillar; and depositing a metal layer over the apertured electrically-conductive layer to provide an apertured microneedle.

In some embodiments, the mold pillar extends away from a surface of a substrate. The mold pillar may extend away from the surface of the substrate in a direction generally normal to the surface of the substrate. The mold pillar may comprise a photoresist and providing the mold pillar may comprise exposing the photoresist to actinic radiation through a mask. The mask may comprise a circular-shaped region which is transparent to actinic radiation. The mold pillar may comprise a cone-shaped mold pillar with a base and a tip. Providing the mold pillar may comprise using an etching process to sharpen the tip of the mold pillar. In some embodiments the mold pillar comprises a protective layer for protecting the mold pillar from subsequent processes and enabling use of the mold pillar for fabricating a plurality of microneedles. The method may comprise forming the protective layer using a solvent-casting process.

In some embodiments forming the apertured electrically-conductive layer over the mold pillar comprises using a solvent-casting process. Solvent-casting the electrically-conductive layer may comprise adding a polymer and conductive particles to a solvent. The polymer may comprise poly(methyl methacrylate) (PMMA) and the conductive particles may comprise carbon black particles. The method may comprise adding a surfactant to the solvent. The apertured electrically-conductive layer may comprise a uniform distribution of the conductive particles within the polymer. Forming the apertured electrically-conductive layer over the mold pillar may comprise coating the mold pillar with the electrically-conductive layer and then removing a portion of the electrically-conductive layer to form an aperture. The method may comprise removing the portion of the electrically-conductive layer by dry etching. The method may comprise removing the portion of the electrically-conductive layer by photolithography. The method may comprise removing the portion of the electrically-conductive layer by mechanical grinding. The method may comprise removing the portion of the electrically-conductive layer by localized heating. The method may further comprise forming the apertured electrically-conductive layer by applying a coating to a region of the mold pillar and solvent-casting the electrically-conductive layer onto the mold pillar using a solvent that is repelled by the coating so that the electrically-conductive layer is created with an aperture located at the coated region. The coating may comprise a polar coating and the solvent may comprise a non-polar solvent, or the coating is a non-polar coating and the solvent is a polar solvent. The method may further comprise forming the apertured electrically-conductive layer by orienting the mold pillar so that a first region of the mold pillar is vertically higher than a second region of the mold pillar and solvent-casting the electrically-conductive layer onto the mold pillar so that the force of gravity causes the electrically-conductive layer to form with an aperture at the first region.

In some embodiments, depositing the metal layer over the apertured electrically-conductive layer comprises electroplating the metal layer onto the apertured electrically-conductive layer and using the apertured electrically-conductive layer as an electrode in the electroplating process. The metal layer may comprise a first sub-layer of metal adjacent the electrically-conductive layer and second sub-layer of metal adjacent the first layer of metal. The first sub-layer of metal may comprise a structural metal and the second sub-layer of metal may comprise a biocompatible metal; or the first metal sub-layer may comprise a biocompatible metal and the second metal sub-layer may comprise a structural metal.

In some embodiments, the method may comprise removing the microneedle from the mold pillar. Removing the microneedle from the mold pillar may comprise at least partially dissolving the apertured electrically-conductive layer. Removing the microneedle from the mold pillar may comprise at least partially dissolving a sacrificial layer formed over the mold pillar. The sacrificial layer may be formed between the mold pillar and the apertured electrically conductive layer. Removing the microneedle from the mold pillar may leave the mold pillar substantially intact. The method may further comprise re-using the mold pillar to fabricate a second microneedle. Re-using the mold pillar to fabricate the second microneedle may comprise forming a second apertured electrically-conductive layer over the mold pillar and depositing a second metal layer over the second apertured electrically-conductive layer to provide the second microneedle. Re-using the mold pillar to fabricate the second microneedle may comprise depositing a second metal layer over the apertured electrically-conductive layer to provide the second microneedle.

In some embodiments the method further comprises applying a coating to the microneedle. The coating may comprise a biocompatible coating. The coating may comprise an electrically-insulating coating. The method may comprise removing the microneedle from the mold pillar and applying the coating to an interior surface of the microneedle, the interior surface of the microneedle masked by the mold pillar prior to removal of the microneedle from the mold pillar. The method may comprise forming a sacrificial layer over the mold pillar. Depositing the first metal layer over the mold pillar comprises sputtering the first metal layer over the sacrificial layer. Removing the first microneedle from the mold pillar may comprise at least partially dissolving the sacrificial layer. The coating may comprise metal. Applying the metal coating to the interior surface of the microneedle may comprise electroplating the metal coating over the interior surface of the microneedle and using the microneedle as an electrode in the electroplating process. The coating may comprise a biocompatible coating.

Another aspect of the invention provides a method for fabricating a first microneedle and a second microneedle. The method comprises: providing a mold pillar; depositing a first metal layer over the mold pillar to provide a first microneedle; removing the first microneedle from the mold pillar; and depositing a second metal layer over the mold pillar to provide a second microneedle.

In some embodiments, the mold pillar extends away from a surface of a substrate. The mold pillar may extend away from the surface of the substrate in a direction generally normal to the surface of the substrate. The mold pillar may comprise a photoresist and providing the mold pillar may comprise exposing the photoresist to actinic radiation through a mask. The mask may comprise a circular-shaped region which is transparent to actinic radiation. The mold pillar may comprise a cone-shaped mold pillar with a base and a tip. Providing the mold pillar may comprise using an etching process to sharpen the tip of the mold pillar. In some embodiments the mold pillar comprises a protective layer for protecting the mold pillar from subsequent processes and enabling use of the mold pillar for fabricating a plurality of microneedles. The method may comprise forming the protective layer using a solvent-casting process.

In some embodiments, depositing a first metal layer over the mold pillar to provide the first microneedle comprises forming an electrically-conductive layer over the mold pillar; and depositing the first metal layer over the electrically-conductive layer. Forming the electrically-conductive layer over the mold pillar may comprise using a solvent-casting process. Solvent-casting the electrically-conductive layer may comprise adding a polymer and conductive particles to a solvent. The polymer may comprise poly(methyl methacrylate) (PMMA) and the conductive particles may comprise carbon black particles. The method may comprise adding a surfactant to the solvent. The electrically-conductive layer may comprise a uniform distribution of the conductive particles within the polymer. The electrically-conductive layer may comprise an apertured electrically-conductive layer. The method may further comprise forming the apertured electrically-conductive layer by coating the mold pillar with the electrically-conductive layer and then removing a portion of the electrically-conductive layer to form an aperture. The method may comprise removing the portion of the electrically-conductive layer by dry etching. The method may comprise removing the portion of the electrically-conductive layer by photolithography. The method may comprise removing the portion of the electrically-conductive layer by mechanical grinding. The method may comprise removing the portion of the electrically-conductive layer by localized heating. Forming the electrically-conductive layer over the mold pillar may comprise applying a coating to a region of the mold pillar and solvent-casting the electrically-conductive layer onto the mold pillar using a solvent that is repelled by the coating so that the electrically-conductive layer is created with an aperture located at the coated region. The coating may comprise a polar coating and the solvent may comprise a non-polar solvent, or the coating may comprise a non-polar coating and the solvent may comprise a polar solvent. Forming the apertured electrically-conductive layer over the mold pillar may comprise orienting the mold pillar so that a first region of the mold pillar is vertically higher than a second region of the mold pillar and solvent-casting the electrically-conductive layer onto the mold pillar so that the force of gravity causes the electrically-conductive layer to form with an aperture at the first region.

In some embodiments, depositing the first metal layer over the electrically conductive layer comprises using the electrically-conductive layer as an electrode and electroplating the first metal layer onto the electrically-conductive layer. The first metal layer may comprise a first metal sub-layer applied over the electrically-conductive layer and a second metal sub-layer applied over the first metal sub-layer. The first metal sub-layer may comprise a structural metal and the second metal sub-layer may comprise a biocompatible metal.

In some embodiments, removing the first microneedle from the mold pillar comprises at least partially dissolving the electrically-conductive layer. Removing the first microneedle from the mold pillar may comprise at least partially dissolving a sacrificial layer formed over the mold pillar. The method may comprise forming a sacrificial layer between the mold pillar and the electrically-conductive layer and removing the first microneedle from the mold pillar may comprise at least partially dissolving the sacrificial layer. Removing the first microneedle from the mold pillar may leave the mold pillar substantially intact. The method may further comprise applying a coating to the first microneedle. The coating may comprise a biocompatible coating. The coating may comprise an electrically-insulating coating. The method may comprise, after removing the first microneedle from the mold pillar, applying a coating to an interior surface of the first microneedle, the interior surface of the first microneedle masked by the mold pillar prior to removal of the first microneedle from the mold pillar. The coating may comprise metal. Applying the metal coating to the interior surface of the first microneedle may comprise electroplating the metal coating over the interior surface of the first microneedle using the first microneedle as an electrode in the electroplating process. The coating may comprise a biocompatible coating. Depositing the second metal layer over the mold pillar to provide the second microneedle may comprise depositing the second metal layer over the electrically-conductive layer to provide the second microneedle.

Depositing the second metal layer over the mold pillar to provide the second microneedle may comprise forming a second electrically-conductive layer over the mold pillar and depositing the second metal layer over the second electrically-conductive layer to provide the second microneedle.

Another aspect of the invention provides a method for fabricating a microneedle. The method comprises providing a mold pillar; forming an electrically-conductive polymer layer over the mold pillar; and depositing a metal layer over the electrically-conductive polymer layer to provide a microneedle.

In some embodiments, the mold pillar extends away from a surface of a substrate. The mold pillar may extend away from the surface of the substrate in a direction generally normal to the surface of the substrate. The mold pillar may comprise a photoresist and providing the mold pillar may comprise exposing the photoresist to actinic radiation through a mask. The mask may comprise a circular-shaped region which is transparent to actinic radiation. The mold pillar may comprise a cone-shaped mold pillar with a base and a tip. Providing the mold pillar may comprise using an etching process to sharpen the tip of the mold pillar. In some embodiments the mold pillar comprises a protective layer for protecting the mold pillar from subsequent processes and enabling use of the mold pillar for fabricating a plurality of microneedles. The method may comprise forming the protective layer using a solvent-casting process.

In some embodiments forming the electrically-conductive polymer layer over the mold pillar comprises using a solvent-casting process. Solvent-casting the electrically-conductive polymer layer may comprise adding a polymer and conductive particles to a solvent. The polymer may comprise poly(methyl methacrylate) (PMMA) and the conductive particles may comprise carbon black particles. The method may comprise adding a surfactant to the solvent. The electrically-conductive polymer layer may comprise a uniform distribution of the conductive particles within the polymer. The electrically-conductive polymer layer may comprise an apertured electrically-conductive polymer layer. The method may comprise forming the apertured electrically-conductive polymer layer by coating the mold pillar with the electrically-conductive polymer layer and then removing a portion of the electrically-conductive polymer layer to form an aperture. The method may comprise removing the portion of the electrically-conductive polymer layer by dry etching. The method may comprise removing the portion of the electrically-conductive polymer layer by photolithography. The method may comprise removing the portion of the electrically-conductive polymer layer by mechanical grinding. The method may comprise removing the portion of the electrically-conductive polymer layer by localized heating. The method may comprise forming the apertured electrically-conductive polymer layer by applying a coating to a region of the mold pillar and solvent-casting the electrically-conductive polymer layer onto the mold pillar using a solvent that is repelled by the coating so that the electrically-conductive polymer layer is created with an aperture located at the coated region. The coating may comprise a polar coating and the solvent may comprise a non-polar solvent, or the coating may comprise a non-polar coating and the solvent may comprise a polar solvent. The method may further comprise forming the apertured electrically-conductive polymer layer over the mold pillar by orienting the mold pillar so that a first region of the mold pillar is vertically higher than a second region of the mold pillar and solvent-casting the electrically-conductive polymer layer onto the mold pillar so that the force of gravity causes the electrically-conductive polymer layer to form with an aperture at the first region.

In some embodiments, depositing the metal layer over the electrically-conductive layer comprises electroplating the metal layer onto the electrically-conductive polymer layer and using the electrically-conductive polymer layer as an electrode in the electroplating process. Depositing the metal layer over the electrically-conductive polymer layer may comprise sputtering the metal layer onto the electrically-conductive polymer layer. The metal layer may comprise a first sub-layer of metal adjacent the electrically-conductive polymer layer and second sub-layer of metal adjacent the first layer of metal. The first sub-layer of metal may comprise a structural metal and the second sub-layer of metal may comprise a biocompatible metal; or the first metal sub-layer may comprise a biocompatible metal and the second metal sub-layer may comprise a structural metal.

In some embodiments, the method comprises removing the microneedle from the mold pillar. Removing the microneedle from the mold pillar may comprise at least partially dissolving the electrically-conductive polymer layer. Removing the microneedle from the mold pillar may comprise at least partially dissolving a sacrificial layer formed over the mold pillar. The sacrificial layer may be formed between the mold pillar and the electrically-conductive polymer layer. Removing the microneedle from the mold pillar may leave the mold pillar substantially intact. The method may further comprise re-using the mold pillar to fabricate a second microneedle. Re-using the mold pillar to fabricate the second microneedle may comprise forming a second electrically-conductive polymer layer over the mold pillar and depositing a second metal layer over the second electrically-conductive polymer layer to provide the second microneedle. Re-using the mold pillar to fabricate the second microneedle may comprise depositing a second metal layer over the electrically-conductive polymer layer to provide the second microneedle.

In some embodiments, the method further comprises applying a coating to the microneedle. The coating may comprise a biocompatible coating. The coating may comprise an electrically-insulating coating. The method may further comprise removing the microneedle from the mold pillar; and applying the coating to an interior surface of the microneedle, the interior surface of the microneedle masked by the mold pillar prior to removal of the microneedle from the mold pillar. The coating may comprise metal. Applying the metal coating to the interior surface of the microneedle may comprise electroplating the metal coating over the interior surface of the microneedle and using the microneedle as an electrode in the electroplating process. The coating may comprise a biocompatible coating.

In addition to the exemplary aspects and embodiments described above, further aspects and embodiments will become apparent by reference to the drawings and by study of the following detailed descriptions.

BRIEF DESCRIPTION OF THE DRAWINGS

Exemplary embodiments are illustrated in referenced figures of the drawings. It is intended that the embodiments and figures disclosed herein are to be considered illustrative rather than restrictive.

DESCRIPTION

Throughout the following description specific details are set forth in order to provide a more thorough understanding to persons skilled in the art. However, well known elements may not have been shown or described in detail to avoid unnecessarily obscuring the disclosure. Accordingly, the description and drawings are to be regarded in an illustrative, rather than a restrictive, sense.

One embodiment of the invention provides a method for manufacturing a metallic microneedle. The method may comprise: providing a mold pillar; forming an electrically-conductive layer over the mold pillar; depositing a metal layer over the electrically-conductive layer to provide a microneedle; and removing the microneedle from the mold pillar. The electrically-conductive layer may be apertured prior to deposition of the electrically conductive layer to form an apertured metal layer and a correspondingly apertured microneedle. The mold pillar may be reused to fabricate additional metallic microneedles.

Fabricating or Otherwise Providing a Mold Pillar

A mold pillar may be fabricated by any suitable method including micromachining (e.g. silicon micromachining), embossing (e.g. hot embossing), lithography (e.g. soft lithography and optical lithography), 3D printing and/or the like. The mold pillar may comprise any suitable material. In some embodiments, a previously fabricated microneedle may be used as the mold pillar.

The mold pillar may have any suitable shape and may comprise a column, post, cone, wall, etc. The mold pillar may be fabricated to extend away from (or may otherwise extend away from) a substrate. The substrate may comprise any suitable material including silicon, glass, Pyrex®, quartz, polymer, metal, ceramic, and any combination thereof. The mold pillar may extend from the surface of the substrate in any direction(s) including, where the substrate is generally planar, in out-of-plane directions (e.g. in direction (s) which have at least a component that is normal to the generally planar surface of the substrate). In embodiments, where the substrate is non-planar, the mold pillar may extend in direction(s) which have at least a component that is normal to the surface of the substrate at the location of the mold pillar. An array comprising a plurality of mold pillars may be fabricated or otherwise provided on the surface of the substrate. As will become clear from the description that follows, the spacing and arrangement of the array of mold pillars may define the spacing and arrangement of an array of microneedles fabricated using the array of mold pillars.

Figure 1A:
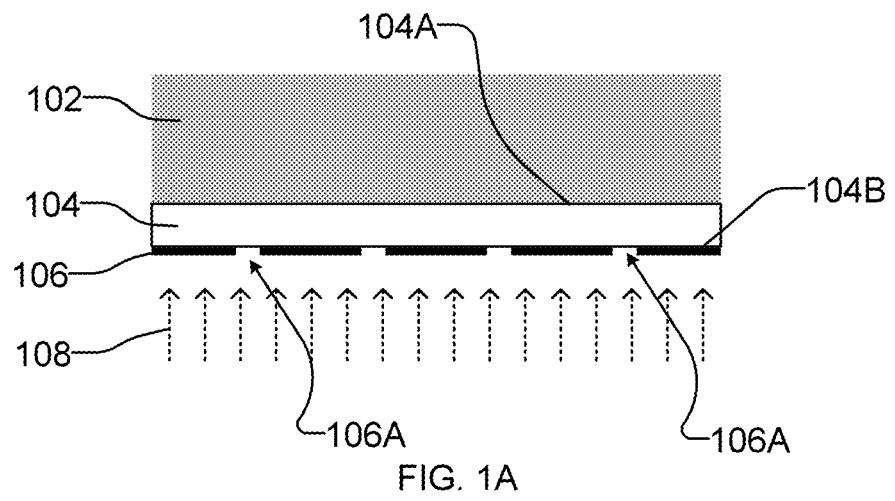
FIGS. 1A-1G (collectively, FIG. 1) are cross-sectional views which depict a method for fabricating metallic microneedle(s) according to example embodiment(s).
Figure 1B:
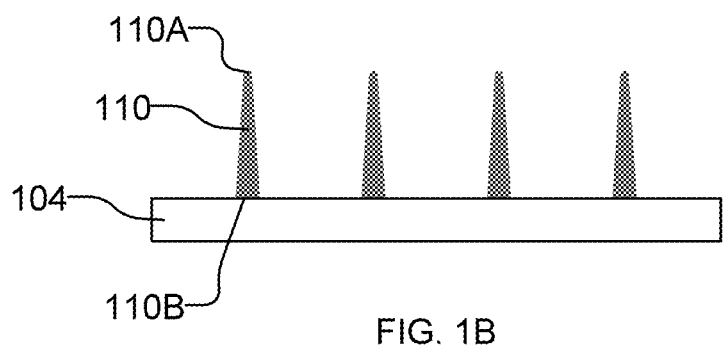

FIGS. 1A and 1B show a method for fabricating an array of mold pillars 110 according to an example embodiment. A photoresist 102 may be applied to a first surface 104A of a substrate 104 and a mask 106 may be applied to the opposing surface 104B of substrate 104. The masked surface 104B of substrate 104 may be exposed to actinic radiation 108. After the exposure to actinic radiation 108, photoresist 102 may be submerged in a developer bath, thereby dissolving some of photoresist 102 and leaving behind mold pillars 110 (FIG. 1B). The illustrated embodiment of FIGS. 1A and 1B involves using a negative photoresist 102 (where exposed photoresist is maintained after exposure to provide mold pillars 110). In some embodiments, a positive photoresist may be used (such that exposed photoresist is dissolved and the non-exposed photoresist is maintained after exposure to provide mold pillars 110).

In some exemplary embodiments, a layer of a thickness in a range of 200 μm-1200 μm (e.g. 700 μm) of SU-8 2150 epoxy-type negative photoresist (from MicroChem® of Newton, Mass.) may be spin-coated (or otherwise coated) onto surface 104A of a substrate 104 comprising a Pyrex™ wafer having a thickness in a range of 100 μm-500 μm (e.g. 300 μm). Substrate 104 and photoresist 102 may be soft-baked for 10 minutes at 65° C. and for 2.5 hours at 95° C. A dark field mask 106 shaped to define arrays of circular-shaped regions transparent to actinic radiation (e.g. apertures) 106A is used to cover masked surface 104B. In some embodiments, the circular-shaped transparent regions 106A have diameters of 20-120 μm (e.g. 40 μm). In some embodiments, transparent regions 106A may have different shapes (e.g. polygonal). In some embodiments, the edges of such polygonal shaped regions may have sizes in a range of 20-120 μm (e.g. 40 μm).

Masked surface 104B of substrate 104 may be exposed to actinic radiation which causes the exposed portions of the SU-8 photoresist to form cross-links. In some embodiments, the actinic radiation comprises ultraviolet radiation. In one particular example embodiment, the actinic radiation is 9200 mJ/cm² of ultraviolet light. After the exposure, the substrate 104 and the photoresist 102 may be baked for 5 minutes at 65° C. and for 35 minutes at 95° C., then placed in a developer bath for 50 minutes to remove the unexposed photoresist 104, then baked for 1 hour at 175° C.

Exposure of the photoresist 102 through transparent regions 106A of mask 106 may result in radiation exposure to cone-shaped portions of photoresist 102 and may thereby create cone-shaped mold pillars 110 after development, wherein such cone-shaped mold pillars 110 comprise bases 110B and tips 110A. This shape may be provided, for example, because of the space (between mask 106 and photoresist 102) provided by exposing photoresist 102 through substrate 104. The bases 110B of cone-shaped mold pillars 110 may have cross-sectional dimensions that are greater than the tips 110A of mold pillars 110. This is not necessary, however. In some embodiments, mold pillars 110 may be shaped such that they have sidewall(s) which extend substantially orthogonally (or in the direction of the normal vector) from the surface of substrate 104 for at least a portion thereof (e.g. a portion near to bases 110B) and may, optionally, be sharper near tips 110A. In some embodiments, mold pillars 110 may have sidewalls with angles that range from 75 to 90 degrees relative to the surface of substrate 104. In some embodiments, mold pillars 110 may have aspect ratios (i.e. ratios of height (e.g. distance between bases 110B and tips 110A) to base dimension (e.g. base diameter, the longest dimension of base 110B and/or the like) that range from 3:1 to 12:1. In other embodiments, mold pillars 110 may have other sidewall angles and other aspect ratios.

As explained in more detail below, the cone-shaped mold pillars 110 of the illustrated embodiment may be used to fabricate microneedles with relatively wide channel openings (e.g. near bases 110B of mold pillars 110) and sharp tips (e.g. near tips 110A of cone-shaped mold pillars 110). The diameters/edge-lengths of the bases 110B of cone-shaped mold pillars 110 (and the corresponding diameters/edge-lengths of the channel openings of microneedles fabricated using mold pillars 110) may be approximately equal to the diameters/edge-lengths of the transparent regions 106A of mask 106.

In some embodiments, substrate 104 upon which mold pillars 110 are formed may be cut (or otherwise separated) into smaller pieces (e.g. 1 by 1 cm pieces), with each piece comprising a mold pillar 110 and/or an array of a plurality of mold pillars 110.

Figure 4A:
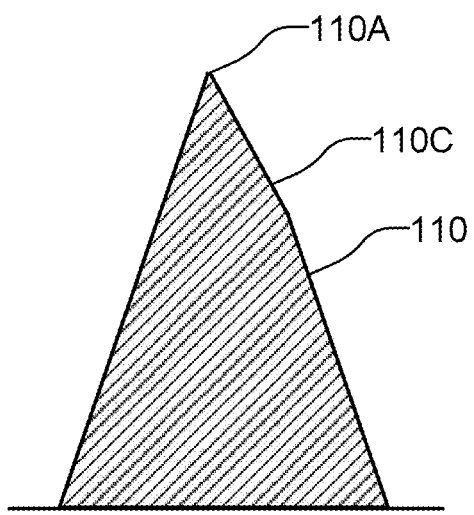
FIG. 4A is a schematic plan view of an asymmetrically shaped mold pillar according to a particular embodiment.

In some embodiments, mold pillars 110 may be further shaped by any suitable method. For example, the tips 110A of mold pillars 110 may be sharpened (e.g. isotropically) using an etching process (e.g. dry etching). In some embodiments, the tips 110A of mold pillars 110 may be sharpened asymmetrically—e.g. to have an asymmetric tip shape similar to the shape 110C of the mold pillar tip 110A shown in FIG. 4A.

Figure 1C:
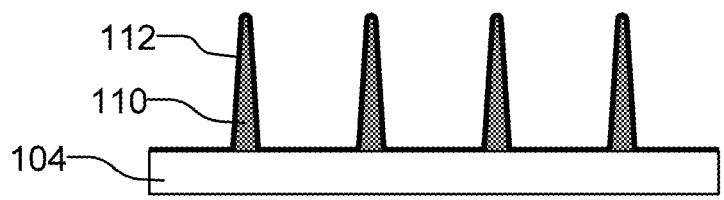

In some embodiments, including the exemplary embodiment of FIG. 1C, a protective layer 112 may be applied to the surfaces of the mold pillars 110 and/or to substrate 104 by any suitable method including sublimation, spray-deposition, condensation, pouring, sputtering, spin-casting, solvent-casting, and/or the like. Such a protective layer 112 may increase the strength of mold pillars 110 and/or the bonding of mold pillars 110 to substrate 104. Protective layer 112 may help to make mold pillars 110 sufficiently durable to be reused multiple times to make multiple sets of microneedles. Protective layer 112 is optional and not necessary. In some embodiments, mold pillars 110 may be sufficiently durable to be reused multiple times to make microneedles even without protective layer 112. Protective layer 112 may comprise any suitable material. Protective layer 112 may comprise the same material or a different material as mold pillar 110.

FIG. 1C shows an example method for coating mold pillars 110 and substrate 104 with a protective layer 112. Protective layer 112 may be applied by dissolving the material of protective layer 112 in a solvent to form a solution, and then casting (e.g. solvent casting and/or spin casting) the solution onto mold pillars 110 and substrate 104. The solvent may be evaporated, leaving behind protective layer 112. Protective layer 112 may be cured with light, heat and/or the like.

In one particular and non-limiting embodiment, SU-8 3025 (from MicroChem® of Newton, Mass.) may be diluted with cyclopentanone to make a 6.7 wt % solution. This solution may be cast (e.g. solvent cast and/or spin cast) onto mold pillars 110 and/or substrate 104 for 20 minutes at 95° C. leaving a 30 μm protective layer 112. This protective layer 112 may be cured with 900 mJ/cm² of ultraviolet light and baked for 5 minutes at 95° C. and for 1 hour at 190° C.

Forming an Electrically-Conductive Layer Over the Mold Pillar

After fabricating or otherwise providing mold pillar 110, the exposed surface of mold pillar 110 may be coated with an electrically-conductive layer 114 by any suitable method including, by way of non-limiting example, sublimation, spray-deposition, condensation, pouring, spin-casting, solvent-casting, sputtering and/or the like. If mold pillar 110 has a protective layer 112, the exposed surface of protective layer 112 may be coated with the electrically-conductive layer 114. In some embodiments, mold pillar 110 or protective layer 112 may be first coated with a sacrificial layer (i.e. a layer that may later be dissolved, melted, or otherwise destroyed), and then the exposed surface of the sacrificial layer may be coated with conductive layer 114. In some embodiments, conductive layer 114 itself may provide a sacrificial layer (as discussed in more detail below).

Conductive layer 114 may comprise any suitable material. In some embodiments, conductive layer 114 comprises one or more conductive polymers. Conductive layers 114 comprising conductive polymers may comprise one or more intrinsically or natively conductive polymers (e.g. poly(3,4-ethylene-dioxythiophene)); conductive co-polymers (e.g. the copolymer of poly(3,4-ethylenedioxythiophene) and poly(styrene-sulfonate)); and polymers containing conductive particles to form conductive composite polymer matrices. By way of non-limiting example, polymers that may be used in conductive composite polymer matrices include:
- poly(methyl methacrylate) (PMMA);
- poly(vinyl acetate);
- polyacrylonitrile;
- poly(vinyl chloride);
- poly(vinylidene chloride);
- polyethylene (LDPE, HDPE);
- polypropylene;
- polystyrene;
- polytetrafluoroethylene;
- biodegradable polymers and copolymers (e.g. poly(lactic acid), poly(lactic-co-glycolic acid), poly(caprolactone), polyphosphazenes, and polyanhydrides);
- biopolymers (e.g. polysaccharides (e.g. chitosan and cellulose), polypeptides and polynucleotides); and/or
- the like.

Conductive particles that may be used in conductive composite polymer matrices include carbon black (CB) particles, metal particles (e.g. silver nanoparticles), metal oxide particles, particles comprising conductive polymers, and/or the like. In some embodiments, conductive layer 114 may comprise one or more suitable metals or alloys thereof.

Figure 1D:
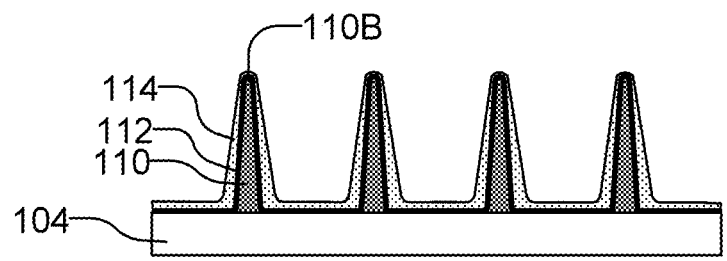

FIG. 1D shows an example method for coating one or more mold pillars 110 with a conductive layer 114. In the illustrated embodiment, mold pillars 110 comprise protective layer 112, although (as discussed above), this is not necessary and conductive layer 114 may be formed over mold pillars 110 without protective layer 112. In some embodiments, conductive layer 114 is solvent-cast. Conductive layer 114 may be applied by first dissolving the material of conductive layer 114 in a solvent to form a solution, then casting the solution onto mold pillars 110 (e.g. onto protective layer 112 in the case of the illustrated embodiment). The solvent may be evaporated, leaving behind conductive layer 114 on mold pillars 110. In the FIG. 1D embodiment, mold pillars 110 are oriented so that they extend away from substrate 104 in a direction that is opposed to the force of gravity—i.e. tips 110A of mold pillars 110 are located above substrate 104. The force of gravity may cause the conductive layer solution to form a relatively thin layer at tips 110A and a relatively thick layer closer to bases 110B. Consequently, in some embodiments, conductive layer 114 may be relatively thin or even absent at tips 110A. The solvent-casting parameters (e.g. concentration, temperature, dew point, evaporation rate, humidity, etc.) may be adjusted to control the thickness of conductive layer 114 (e.g. the thickness of conductive layer 114 between tips 110A and bases 110B of mold pillars 110).

In some exemplary embodiments, the conductive layer 114 may comprise PMMA (from Polysciences® of Warrington, Pa.), with molecular weight of 25 kDa, seeded with carbon black (CB, VULCAN® XC72R, from Cabot® Corporation of Boston, Mass.), with a primary particle size of about 150 nm A PMMA/CB solution/suspension may be prepared by adding 0.3 g of PMMA and 0.135 g of CB to a carrier fluid comprising 5 g of N-methyl-2-pyrrolidone (NMP). In some embodiments, other suitable carrier fluids may be used. By way of non-limiting example, suitable carrier fluids may include dimethylformamide (DMF), dimethylsulfoxide (DMSO), longer chain alcohols including 1-octanol, and/or the like.

A surfactant comprising 0.015 g of sodium dodecyl sulfate (SDS, from Sigma-Aldrich® of Oakville, ON) may be added to the conductive polymer solution/suspension. The solution/suspension may be placed in an ultrasonic bath for 30 minutes. The resulting fluid may have a solid concentration of 9 wt % with CB accounting for 30% of the total solid content. This fluid may be applied to mold pillars 110 (e.g. onto protective layer 112 in the case of the illustrated embodiment) and substrate 104 and allowed to evaporate to leave behind a conductive layer comprising a polymer matrix of PMMA and CB.

The surfactant may help to prevent the formation of CB particle clusters and may thereby result in a relatively uniform distribution of the CB particles in the solution/suspension. Uniform suspension of the CB particles in the solution/suspension may result in uniform distribution of the CB particles within the PMMA polymer matrix once the material is cast onto mold pillars 110 and substrate 104. The uniform distribution of CB particles within the PMMA polymer matrix may result in conductive layer 114 having uniform conductivity. As discussed in more detail below, this uniform conductivity of conductive layer 114 may in turn facilitate deposition, by electroplating, of a uniform metal layer 118 over conductive layer 114.

Any suitable surfactant may be used in the conductive polymer solution/suspension. By way of non-limiting example, suitable surfactants may comprise:
- non-ionic surfactants including:
  - polyoxyethylene glycol octylphenol ethers (Triton X-100),
  - glucoside allyl ethers (lauryl glucoside),
  - sorbitan alkyl esters (spans),
  - copolymers of polyethylene glycol,
  - polypropylene glycol (poloxamers), and/or
  - the like;
- anionic surfactants including:
  - sodium dodecyl sulfate,
  - ammonium lauryl sulfate,
  - sodium lauryl sulfate,
  - alkyl-aryl ether phosphates,
  - alkyl ether phosphates,
  - dioctyl sodium sulfosuccinate,
  - perfluorooctanesulfonate, and/or
  - the like;
- cationic surfactants including:
  - cetyl trimethylammonium bromide,
  - cetylpyridinium chloride, and
  - dimethyldioctadecylammonium chloride, and/or
  - the like; and
- zwitterionic surfactants including:
  - lecithin (phosphatidyl choline),
  - CHAPS (3-[(3-cholamidopropyl)dimethylammonio]-1-propanesulfonate), and/or
  - the like; and/or
- the like.

In some embodiments, a substance may be applied to mold pillars 110 and/or substrate 104 (or protective layer 112 or the sacrificial layer, if present) to improve surface adhesion before applying conductive layer 114. For example, in one particular example embodiment, 20 µl of hexamethyldisilazane (HMDS, from Sigma-Aldrich® of Oakville, ON) may be applied to mold pillars 110 (e.g. onto protective layer 112 in the case of the illustrated embodiment) and substrate 104 at room temperature. Then, 40 µl of the 9 wt % PMMA/CB mixture may be deposited onto mold pillars 110 and substrate 104 and then baked for 3 hours at 80° C. to evaporate the NMP and fully dry the PMMA/CB mixture. The resulting layer of PMMA/CB may be 100 µm thick on substrate 104 and may gradually decrease in thickness towards tips 110A of mold pillars 110.

In some embodiments conductive layer 114 may be apertured to provide apertured conductive layer 114A. In this description, use of the term conductive layer 114 may (but need not necessarily) include apertured conductive layer 114A, as the context dictates. Apertured conductive layer 114A may be used to fabricate hollow microneedles (i.e. microneedles with apertures therethrough). A solid (i.e. non-apertured) conductive layer 114 may be used to fabricate solid (i.e. non-apertured) microneedles.

Any suitable method may be used to form apertured conductive layer 114A having or defining one or more apertures 117 therethrough. Any suitable method may be used to make or create one or more apertures 117 in a conductive layer 114 that is already formed to provide apertured conductive layer 114A.

Figure 4B:
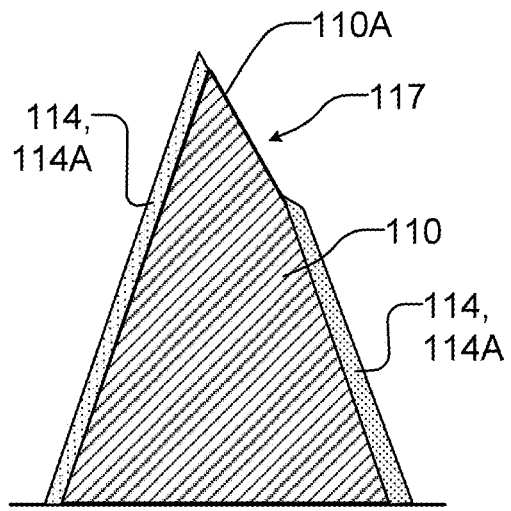
FIG. 4B is a schematic plan view of an asymmetrically shaped aperture formed in an electrically conductive layer according to a particular embodiment.

An aperture 117 through apertured conductive layer 114A may be located anywhere on apertured conductive layer 114A. In some embodiments, apertures 117 are located on apertured conductive layer 114A in regions corresponding to mold pillars 110. For example, apertures 117 may extend through apertured conductive layer 114A to expose the surfaces of mold pillars 110 or may extend through apertured conductive layer 114A in regions corresponding to (e.g. covering) mold pillars 110, as opposed to regions between mold pillars 110. In some embodiments, an aperture 117 may be located at the tip 110A of mold pillar 110. In some embodiments, an aperture 117 may be symmetrically shaped at tip 110A of mold pillar 110. In some embodiments, an aperture 117 may be asymmetrically shaped at tip 110A of mold pillar 110 in a manner similar to that shown in FIG. 4B.

In some embodiments, an aperture 117 may be made in an already-formed conductive layer 114 using a suitable etching technique to provide apertured conductive layer 114A. Suitable etching techniques may include chemical etching, physical etching, plasma etching, reactive ion etching and/or the like. In some embodiments, an aperture 117 may be made in an already-formed conductive layer 114 using laser ablation to provide apertured conductive layer 114A.

Figure 1E:
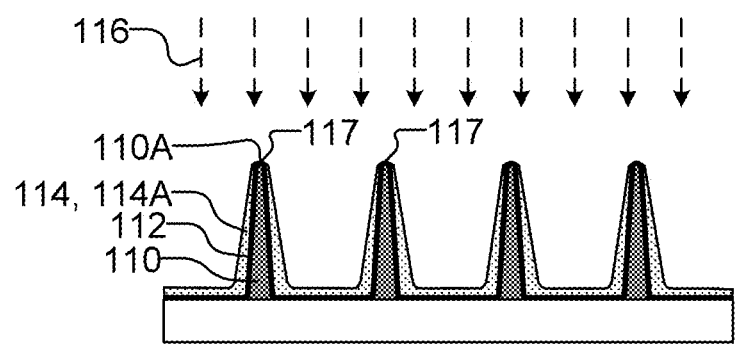

FIG. 1E shows an example method for removing conductive layer 114 from tips 110A of mold pillars 110 to form apertures 117 that extend through conductive layer 114 in regions corresponding to mold pillars 110 (more particularly, to tips 110A of mold pillars 110) and to thereby provide apertured conductive layer 114A. Conductive layer 114 may be bombarded by ions 116 in the general direction shown by arrows in FIG. 1E. Ions 116 may wear away conductive layer 114 until apertures 117 are formed and tips 110A of mold pillars 110 (or the portions of protective layer 112 covering tips 110A) are exposed to thereby provide apertured conductive layer 114A. The etching process may cause tips 110A to have higher temperatures than other portions of mold pillars 110. Mold pillars 110 may have poor thermal conductivity and this may contribute to the temperature differential. The higher temperature of tips 110A may cause an increased etching rate at tips 110A compared to at other portions of mold pillars 110.

In some embodiments, the portion of conductive layer 114 covering the tip 110A of a mold pillar 110 (or some other portion of conductive layer 114 that covers mold pillar 110)

may be removed to make apertures 117 by plasma etching to thereby provide apertured conductive layer 114A. By way of non-limiting example, the plasma may comprise $O_2/CF_4$ ($O_2$ flow rate: 80 sccm; $CF_4$ flow rate: 20 sccm; pressure: 500 mTorr; temperature: 25° C.; power: 200 W). The plasma may be applied for a suitable duration (e.g. 200 seconds) or until conductive layer 114 is removed from the tip 110A of mold pillar 110 to provide apertures 117 and to thereby provide apertured conductive layer 114A.

In some embodiments, portions of conductive layer 114 may be removed to make apertures 117 (and to thereby provide apertured conductive layer 114A) by mechanical grinding, laser micromachining or by localized heating.

In some embodiments, conductive layer 114 may comprise a photo-patternable polymer and portions of conductive layer 114 may be removed to form apertures 117 by photolithography to thereby provide apertured conductive layer 114A.

In some embodiments, conductive layer 114 may be applied using solvent-casting and various solvent-casting parameters (e.g. concentration, temperature, dew point, evaporation rate, humidity, etc.) may be adjusted so that portions of mold pillars 110 are not coated with conductive layer 114 when the solvent is evaporated—i.e. such that apertures 117 are formed through conductive layer 114 as conductive layer 114 is applied to mold pillars 110 to thereby provide apertured conductive layer 114A. For example, the concentration of a polymer or a surfactant in the conductive polymer solution used to apply conductive layer 114 may be adjusted so that conductive layer 114 does not form in regions corresponding to the tips 110A of mold pillars 110, thereby providing apertures 117 through conductive layer 114 in the vicinities of tips 110A to thereby provide apertured conductive layer 114A.

In some embodiments, a portion of the surface of a mold pillar 110 may be chemically or physically modified to change its wetting behavior, so that a solvent-cast conductive layer 114 may be formed with an aperture 117 to thereby provide apertured conductive layer 114A. If, for example, conductive layer 114 is solvent-cast using a polar solvent, then a non-polar coating (not shown) may be applied to the tip 110A of mold pillar 110 (or to some other region of mold pillar 110 where it is desired to provide an aperture 117), so that conductive layer 114 does not wet (or adhere to) the region (e.g. the tip 110A) of mold pillar 110 that is coated with the non-polar coating. If, for example, a conductive layer 114 is solvent-cast using a non-polar solvent, then a polar coating (not shown) may be applied to the 110A tip of mold pillar 110 (or to some other region of mold pillar 110 where it is desired to provide an aperture 117), so that conductive layer 114 does not wet (or adhere to) the region (e.g. the tip 110A) of mold pillar 110 that is coated with the polar coating.

In some embodiments, where conductive layer 114 is applied by solvent casting using a water-based solvent, hydrophobic nanoparticles may be deposited onto the tip 110A of mold pillar 110 (or to some other region of mold pillar 110 where it is desired to provide an aperture 117) before conductive layer 114 is applied to mold pillar 110. Any suitable type of hydrophobic material may be used including, by way of non-limiting example, poly(ethylene-co-tetrafluoroethylene), poly(chlorotrifluoro-ethylene), poly (vinylidene fluoride), poly(vinylidene fluoride-co-hexafluoropropylene), and/or the like. Before the hydrophobic nanoparticles are deposited, the tip 110A of mold pillar 110 may be coated with a thin layer of SU-8, which may help the hydrophobic nanoparticles to adhere to tip 110A. The SU-8 may be applied by stamping, for example.

In one example embodiment, a dry 300 nm diameter polytetrafluoroethylene (PTFE) nanoparticle powder may be mixed into ethanol at a 1:50 weight ratio to form a suspension. The suspension may be deposited onto a stamp using an airbrush. The stamp may comprise a soft piece of polydimethylsiloxane (PDMS), fabricated using standard soft lithography. The airbrush's suspension and airflow rate and the distance between the airbrush and the stamp may be adjusted to ensure that the atomized droplets expelled by the airbrush evaporate upon reaching the stamp. The coated mold pillar 110 may be baked for 2 minutes at 100° C., then a uniform contact may be made between the stamp and the tip of the mold pillar for 10 seconds.

It will be appreciated that in some embodiments, where conductive layer 114 is applied by solvent casting using a non-polar solvent, oleophobic nanoparticles may be deposited onto the tip 110A of mold pillar 110 (or to some other region of mold pillar 110 where it is desired to provide an aperture 117) before conductive layer 114 is applied to mold pillar 110, thereby facilitating the formation of apertured conductive layer 114A in an analogous process.

Depositing Metal Layer(s) Over Electrically-Conductive Layer to Provide a Microneedle One or more metal layers 118 may be deposited onto conductive layer 114 using any suitable method including electroplating, sputtering, and/or the like. In currently preferred embodiments, one or more metal layers 118 are applied to apertured conductive layer 114A using an electroplating technique which creates one or more correspondingly apertured metal layers 118A. In this description, use of the term metal layer 118 may (but need not necessarily) include apertured metal layer 118A, as the context dictates. Metal layer 118 may comprise any suitable metal including, by way of non-limiting example, cobalt, nickel, chromium, manganese, iron, gold, copper, lead, ruthenium, rhodium, palladium, silver, mercury, rhenium, titanium, niobium, tantalum, osmium, iridium, platinum, combinations thereof; and/or the like. Metal layer 118 may provide desirable structural strength to a microneedle 120 fabricated therefrom.

In some embodiments, multiple metal layers 118 may be deposited onto electrically-conductive layer 114. In some embodiments, metals A, B, and C, may be deposited in sequence, so only metals A and C will be exposed in the completed microneedle (assuming that electrically conductive layer 114 is partially or completely removed when the microneedle is removed from mold pillar 110). The encapsulated metal B may be a structural metal and may comprise nickel, for example. The exposed metals A and C may comprise biocompatible metals. The exposed metals A and C may be the same as one another or different from one another. Non-limiting examples of biocompatible metals include: gold, platinum, titanium, CoCr, 316L stainless steel, cobalt-chromium, titanium, titanium-based implant alloys which rely on their passivation by a thin layer of oxide, alloys thereof and/or the like.

Figure 1F:
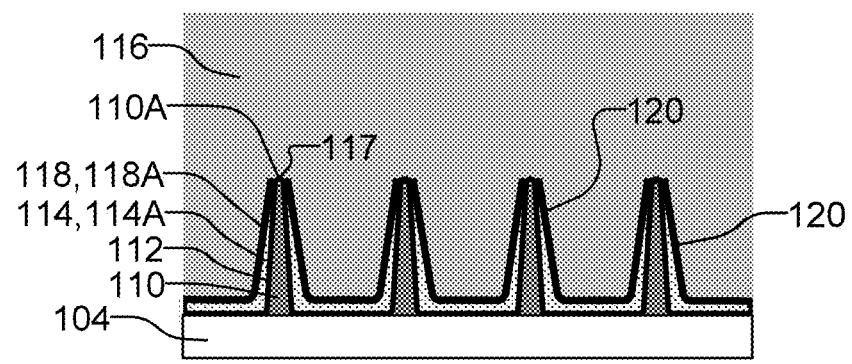

FIG. 1F shows an example method for coating conductive layer 114 with a metal layer 118 by electroplating. More particularly, FIG. 1F shows a method for electroplating a metal layer 118 onto apertured conductive layer 114A to provide apertured metal layer 118A. Conductive layer 114 may be placed in a solution 116 containing metal ions. Conductive layer 114 may be connected as one of two electrodes in solution 116. A voltage may be applied between the electrodes and the metal ions in solution 116 may be electroplated onto conductive layer 114, thereby forming metal layer 118. If conductive layer 114 has an aperture 117 (as is the case in apertured conductive layer 114A in the illustrated embodiment), metal ions are not deposited onto or into aperture 117, thereby forming an apertured metal layer 118A having aperture 117. As mentioned above, in the FIG. 1F embodiment, apertured conductive layer 114A has apertures 117 at tips 110A of mold pillars 110 and, consequently, the FIG. 1F electroplating process forms an apertured metal layer 118A is formed with apertures 117 at tips 110A of mold pillars 110. Metal layer 118 may provide an array of microneedles 120.

In one embodiment, conductive layer 114 may be placed into an electroplating solution. The electroplating solution may comprise nickel chloride, nickel sulfate, and boric acid. Conductive layer 114 may be positioned parallel to and 2.5 cm away from a pure nickel anode. Conductive layer 114 may act as a cathode and may be connected to a power supply by a suitable electrical connection (e.g. a wire). Conductive layer 114 may have a lower conductivity than the electrical connection, and the electrical connection may be kept, for the most part, out of the solution to prevent nickel from accumulating on the electrical connection. The power supply may provide a constant current of 2 mA for 150 minutes. A metal layer 118 of nickel may thereby be formed over conductive layer 114. In some embodiment, metal layer 118 has a thickness in a range of 10 to 200 µm (e.g. 70 µm). In other embodiments, metal layer 118 may have a wider thickness range.

In one embodiment, 0.2 mm diameter platinum wires (from Alfa Aesar® of Ward Hill, Mass.) may be used as anodes. In other embodiments, wires made of other suitable materials may be used as anodes. A Kenwood® PR18-1.2A power supply (from Davis Instruments™ of Baltimore, Md.) may be used to electroplate a first metal layer on the conductive layer. Then, a layer of gold may be electroplated onto the first metal layer using a solution comprising a phosphate buffer at pH7, 0.17 M of $H_3PO_4$, 0.07 M of $KH_2PO_4$, and 0.07 M of $KAu(CN)_2$. The gold may be electroplated for 5 minutes at a current density at 102 A/m². The final thickness of the gold layer may be in a range of 0.05 to 10 µm (e.g. 3 µm).

Removing Microneedle from the Mold Pillar

Microneedle 120 provided by metal layer 118 may be removed from mold pillar 110 by any suitable method. By way of non-limiting example:
- mold pillar 110 may be at least partially dissolved or otherwise depleted until metal layer 118 (and microneedle 120) can be removed from mold pillar 110;
- conductive layer 114 may be at least partially dissolved or otherwise depleted until metal layer 118 (and microneedle 120) can be removed from mold pillar 110;
- conductive layer 114 may have a weak surface bond with metal layer 118, allowing metal layer 118 (and microneedle 120) to be removed mechanically from mold pillar 110;
- conductive layer 114 may be softened or melted by heat treatment until metal layer 118 (and microneedle 120) can be removed mechanically;
- a sacrificial layer may have been formed between mold pillar 110 and conductive layer 114 and:
  - the sacrificial layer may be at least partially dissolved, depleted or destroyed to permit microneedle 120 (including metal layer 118 and possibly some or all of conductive layer 114) to be removed from mold pillar 110;
  - the sacrificial layer may have a weak surface bond with conductive layer 144 to permit mechanical removal of microneedle 120 (including metal layer 118 and possibly some or all of conductive layer 114) from mold pillar 110;
  - the sacrificial layer may be softened or melted by heat treatment to permit microneedle 120 (including metal layer 118 and possibly some or all of conductive layer 114) to be removed from mold pillar 110; and/or
- the like.

The sacrificial layer may be conductive or non-conductive. The sacrificial layer may be made of any suitable material including silicon dioxide, silicon nitride, silicon germanium, and polysilicon. It may be deposited by any suitable method including sublimation, spray deposition, chemical vapor deposition, condensation, pouring, solvent-casting, sputtering, and/or the like.

In embodiments where mold pillar 110 is left intact (or substantially intact) after microneedle 120 is removed, mold pillar 110 may be reused to fabricate additional microneedles.

Where an apertured, electrically-conductive layer 114A was used and a corresponding apertured metal layer 118A is formed upon the apertured electrically conductive later, the removed microneedle 120 may comprise a hollow (or apertured) microneedle 120 (e.g. a microneedle 120 through which fluid may travel). Where a non-apertured, electrically-conductive layer 114 was used, the removed microneedle 120 may comprise a non-apertured microneedle. In some embodiments, a non-apertured microneedle 120 may remain attached to mold pillar 110 and may not be removed from mold pillar 110 prior to use.

Figure 1G:
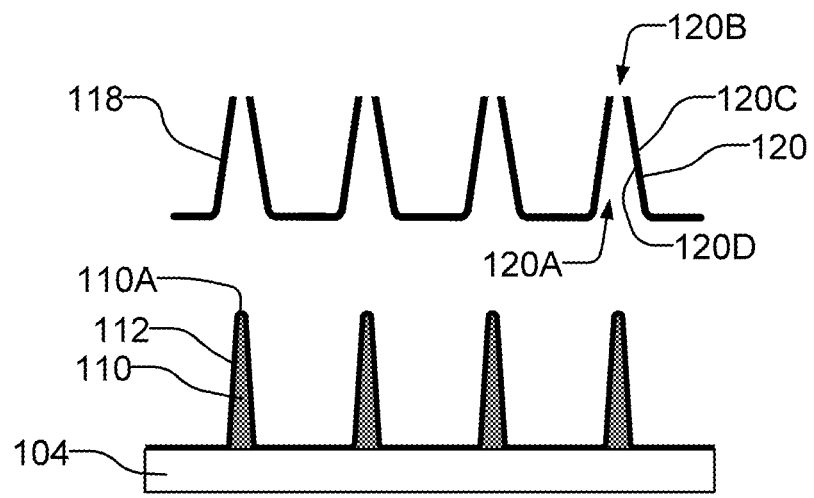

FIG. 1G shows an example method for removing an array of microneedles 120 from mold pillars 110. In the FIG. 1G, conductive layer 114 comprises a sacrificial layer which is at least partially destroyed to remove microneedles 120 from mold pillars 110. Conductive layer 114 may be at least partially dissolved using a suitable solvent (e.g. the same solvent which was used to solvent-cast conductive layer 114 in step of FIG. 1D). Once conductive layer 114 is partially dissolved, the array of microneedles 120 may be removed from mold pillars 110. Microneedles 120 may comprise apertured (or so-called hollow) microneedles 120. As shown in FIG. 1G, microneedles 120 may comprise lumens 120A (which are formed at bases 110B of mold pillars 110), apertures/nozzles 120B (which are formed at tips 110A of mold pillars 110), outside surfaces 120C, and inside surfaces 120D.

In some embodiments, the array of microneedles 120 may be removed from mold pillars 110 by placing conductive layer 114 in an ultrasonic bath of NMP for 60 minutes or until conductive layer 114 dissolves sufficiently for removal of the array of microneedles 120.

A microneedle 120 may have its outside and/or inside surfaces 120C, 120D cleaned (e.g. to remove any remaining electrically-conductive layer 114). A microneedle 120 may have its outside and/or inside surfaces 120C, 120D coated with any suitable coating including polymer coatings and/or metal coatings. Such coatings may be applied by any suitable method including, by way of non-limiting example, electroplating, sputtering, evaporation, chemical vapor deposition and/or the like. Such coatings may be applied before or after microneedle 120 is removed from mold pillar 110. Such coatings may modify the surface properties of microneedle 120. For example, such coatings may make the surface(s) of microneedle 120 hydrophobic, hydrophilic, biocompatible, electrically-insulating and/or the like. Biocompatible coatings may be useful for applications where microneedle 120 is used in applications which puncture the skin or are otherwise used inside of the body of a human or other animal. Non-limiting examples of biocompatible metals include: gold, platinum, titanium, CoCr, 316L stainless steel, cobalt-chromium, titanium, titanium-based implant alloys which rely on their passivation by a thin layer of oxide, alloys thereof and/or the like. Non-metallic biocompatible coatings could also be used, for example, poly (methylmetacrylate). An electrically insulating coating may be beneficial, for example, when microneedle 120 is used as part of an electrochemical sensor. An electrically insulating coating may comprise any suitable material including polyethylene terephthalate, polytetra-fluoroethylene, polyethylene, poly(methyl methacrylate), polylactide, polyglycolide, poly(lactide-co-glycolide) and/or the like.

As discussed above, metal layer 118 provides structural strength to microneedles 120 fabricated therefrom. In some embodiments, microneedles 120 may be strong enough to pierce human skin. Prototype arrays of microneedles 120 were fabricated using the example method depicted in FIGS. 1A-1G. The prototype arrays of microneedles 120 were subject to a series of mechanical compression tests and the results of these tests were compared with literature data. A vertical compressive load was applied to a prototype array of microneedles 120 at a constant velocity of 5 μm/second. Force vs. displacement data were obtained for analysis of failure loads. After each compression test the microneedles 120 were visually inspected to see if the microneedle shafts buckled or if the microneedle tips collapsed.

Five compression tests were conducted and the average failure load was 4.2±0.61 N. For a microneedle 120 with a tip diameter of less than 50 μm (as is the case with the prototype microneedles 120 subjected to the mechanical compression tests), typical forces associated with the penetration of microneedles 120 into human skin are well below 1 N. The failure load of the prototype microneedles was well above 1 N, and therefore the prototype microneedles are strong enough to be inserted into human skin without breaking.

Figure 2:
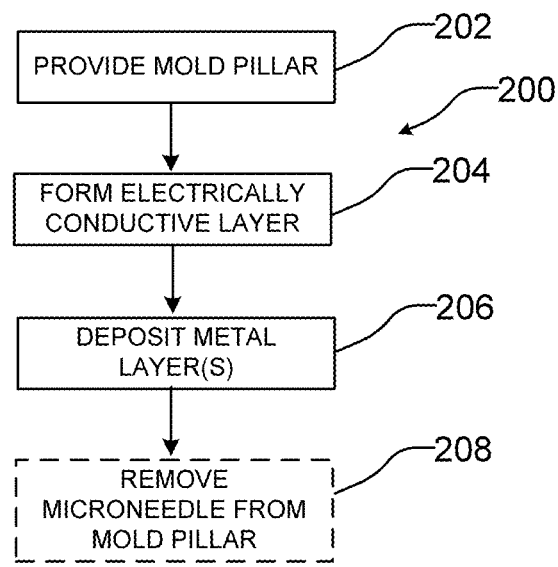
FIG. 2 is a schematic diagram showing a method for fabricating a metallic microneedle according to an example embodiment.

FIG. 2 is a schematic illustration of a method 200 for fabricating a metallic microneedle 120 according to an example embodiment. Method 200 commences in block 202 which comprises fabricating or otherwise providing a mold pillar 110. The block 202 mold pillar 110 may be fabricated or otherwise provided using any of the features, combinations of features or sub-combinations of features described above in connection with providing mold pillars 110 (including, for example, the description of FIGS. 1A, 1B and/or 1C). The block 202 mold pillar 110 may comprise a protective layer 112, which may be considered part of mold pillar 110.

Method 200 then proceeds to block 204 which comprises forming an apertured electrically conductive layer 114A over the block 202 mold pillar 110. Forming the apertured electrically conducting layer 114A may comprise using any of the features, combinations of features or sub-combinations of features described above in connection with forming apertured electrically conductive layer 114A (including, for example, the description of FIGS. 1D and/or 1E). In some exemplary embodiments, apertured electrically conducting layer 114A comprises electrically conductive polymer, which may be applied in block 204 by solvent casting. As discussed above, apertures 117 may be formed on electrically conductive layer 114 as conductive layer 114 is applied to the block 202 mold pillar 110 to provide apertured electrically conductive layer 114A or after conductive layer 114 is applied to the block 202 mold pillar 110 to provide apertured electrically conductive layer 114A.

Method 200 then proceeds to block 206 which comprises depositing a metal layer 118 over the block 204 apertured electrically conductive layer 114A. Depositing the metal layer 118 in block 206 may comprise using any of the features, combinations of features or sub-combinations of features described above in connection with depositing metal layer 118 (including, for example, the description of FIG. 1F). In some exemplary embodiments, metal layer 118 is applied to conductive layer 114 using an electroplating technique. Where conductive layer 114 comprises an apertured conducting layer 114A, electroplating causes the deposition of a corresponding apertured metal layer 118A. In some embodiments, block 206 comprises depositing multiple metal layers 118.

Method 200 may comprise an optional block 208 which involves removing microneedle 120 from mold pillar 110. Removing microneedle 120 in optional block 208 may comprise any of the features, combinations of features or sub-combinations of features described above in connection with removing microneedle 120 from mold pillar 110 (including, for example, the description of FIG. 1G). In some exemplary embodiments, the electrically conductive polymer used to provide apertured conductive layer 114A is at least partially dissolved to permit the block 208 removal of microneedle 120 from mold pillar 110.

Figure 3:
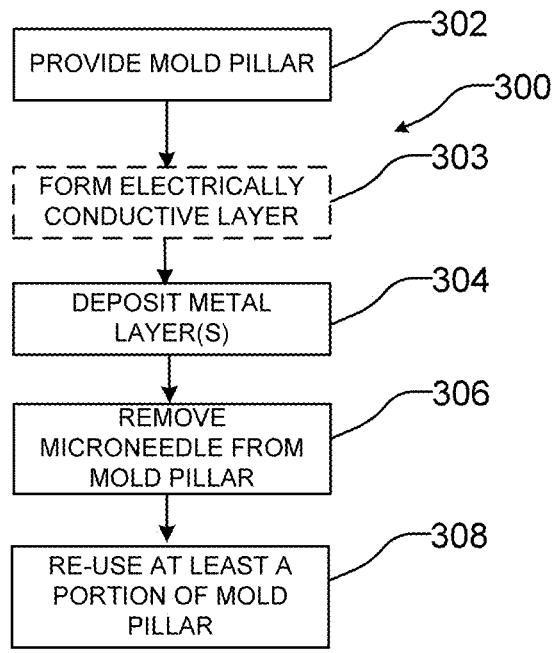
FIG. 3 is a schematic diagram showing a method for fabricating a metallic microneedle according to an example embodiment.

FIG. 3 is a schematic diagram showing a method 300 for fabricating a metallic microneedle 120 according to an example embodiment. Method 300 commences in block 302 which comprises fabricating or otherwise providing a mold pillar 110. Block 302 may be similar to block 202 of method 200 described above. The block 302 mold pillars 110 may comprise electrically conductive layers 114 and block 302 may comprise forming an electrically conductive layer 114 on mold pillar 110 in accordance with any of the features, combinations of features or sub-combinations of features described above in connection with forming electrically conductive layer 114 (including, for example, the description of FIGS. 1D and/or 1E).

In some embodiments, method 300 comprises optional block 303 which comprises forming an electrically conductive layer 114 over the block 302 mold pillar 110. Forming the block 303 electrically conductive layer 114 may comprise using any of the features, combinations of features or sub-combinations of features described above in connection with forming electrically conductive layer 114 (including, for example, the description of FIGS. 1D and/or 1E). In some exemplary embodiments, electrically conductive layer 114 comprises electrically conductive polymer, which may be applied in block 303 by solvent casting. As discussed above, apertures 117 may be formed on electrically conductive layer 114 as conductive layer 114 is applied to the block 302 mold pillar 110 to provide apertured electrically conductive layer 114A or after conductive layer 114 is applied to the block 302 mold pillar 110 to provide apertured electrically conductive layer 114A.

Method 300 then proceeds to block 304 which comprises depositing a metal layer 118 over the block 302 mold pillar 110 and/or the block 303 electrically conductive layer 114. Depositing the metal layer 118 in block 304 may comprise using any of the features, combinations of features or sub-combinations of features described above in connection with depositing metal layer 118 (including, for example, the description of FIG. 1F). In some exemplary embodiments, where the block 302 mold pillar comprises an electrically conductive layer 114, metal layer 118 may be applied to the block 302 mold pillar using an electroplating technique. Where the block 302 mold pillar 110 comprises an apertured conducting layer 114A, electroplating causes the deposition of a corresponding apertured metal layer 118A. In some embodiments, block 304 comprises depositing multiple metal layers 118.

Method 300 then proceeds to block 306 which comprises removing microneedle 120 from mold pillar 110. Removing microneedle 120 in block 306 may comprise any of the features, combinations of features or sub-combinations of features described above in connection with removing microneedle 120 from mold pillar 110 (including, for example, the description of FIG. 1G). In some exemplary embodiments, an electrically conductive polymer used to provide a conductive layer 114 on the block 110 mold pillar is at least partially dissolved to permit the block 306 removal of microneedle 120 from mold pillar 110.

Method 300 then proceeds to block 308 which comprises depositing a second metal layer 118 over the block 302 mold pillar to provide a second microneedle. Block 308 may comprise using at least a portion of the block 302 mold. Block 308 may optionally comprise forming an electrically conductive layer 114 over the block 302 mold pillar 110 (and possibly over any remnants of the block 303 electrically conductive layer 114). Forming such electrically conducting layer may comprise using any of the features, combinations of features or sub-combinations of features described above in connection with forming electrically conductive layer 114 (including, for example, the description of FIGS. 1D and/or 1E). Applying the second metal layer over the mold pillar in block 308 may comprise using any of the features, combinations of features or sub-combinations of features described above in connection with depositing metal layer 118 (including, for example, the description of FIG. 1F).

Figure 5:
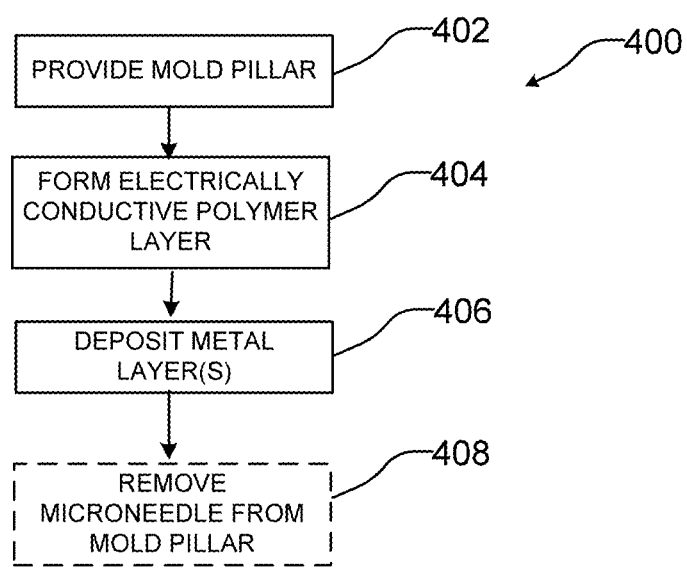
FIG. 5 is a schematic diagram showing a method for fabricating a metallic microneedle according to an example embodiment.

FIG. 5 is a schematic diagram showing a method 400 for fabricating a metallic microneedle 120 according to an example embodiment. Method 400 commences in block 402 which comprises fabricating or otherwise providing a mold pillar 110. Block 402 may be similar to block 202 of method 200 described above.

Method 400 then proceeds to block 404 which comprises forming an electrically conductive layer 114 comprising an electrically conductive polymer over the block 402 mold pillar 110. Forming the block 404 electrically conductive layer 114 may comprise using any of the features, combinations of features or sub-combinations of features described above in connection with forming electrically conductive layer 114, where electrically conductive layer 114 comprises an electrically conductive polymer (including, for example, the description of FIGS. 1D and/or 1E). In some exemplary embodiments, electrically conductive layer 114 may be applied in block 404 by solvent casting. As discussed above, apertures 117 may be formed on electrically conductive layer 114 as electrically conductive layer 114 is applied to the block 402 mold pillar 110 to provide apertured electrically conductive layer 114A or after electrically conductive layer 114 is applied to the block 402 mold pillar 110 to provide apertured electrically conductive layer 114A.

Method 400 then proceeds to block 406 which comprises depositing a metal layer 118 over the block 404 electrically conductive polymer layer 114. Depositing the metal layer 118 in block 406 may comprise using any of the features, combinations of features or sub-combinations of features described above in connection with depositing metal layer 118 (including, for example, the description of FIG. 1F). In some exemplary embodiments, metal layer 118 may be applied to the block 404 electrically conductive polymer layer 114 using an electroplating technique. Where the block 404 electrically conductive polymer layer 114 comprises an apertured electrically conductive polymer layer 114A, electroplating causes the deposition of a corresponding apertured metal layer 118A. In some embodiments, block 406 comprises depositing multiple metal layers 118.

In some embodiments, method 400 comprises optional block 408 which comprises removing microneedle 120 from mold pillar 110. Removing microneedle 120 in block 408 may comprise any of the features, combinations of features or sub-combinations of features described above in connection with removing microneedle 120 from mold pillar 110 (including, for example, the description of FIG. 1G). In some exemplary embodiments, an electrically conductive polymer used to provide a conductive layer 114 on the block 110 mold pillar is at least partially dissolved to permit the block 408 removal of microneedle 120 from mold pillar 110.

Application 1: Delivery Devices

Microneedles 120 may be used for delivery of agents into human or animal tissue, or into plants or soil. Microneedles 120 may be used to deliver any suitable agent including drugs, compounds, particles, and suspensions. Microneedles 120 may be used to deliver vaccines, neurotoxins such as Botox®, and agents for allergy tests.

Hollow (i.e. apertured) microneedles 120 may be used for direct injection of agents. For transdermal injections, a hollow microneedle 120 (or an array of hollow microneedles 120) may pierce the outermost layer of skin (the stratum corneum) and release an agent into the dermal or the epidermal tissue of the skin. In some embodiments, a microneedle 120 may be inserted into skin without damaging or touching nerves so that the insertion is painless or less painful than the insertion of a traditional hypodermal needle. In some embodiments, microneedles 120 may be inserted without touching blood vessels in the dermis.

An array of microneedles 120 (or a single microneedle 120) may be attached to a container, such as a conventional syringe or a microreservoir, containing an agent. A membrane may be moved or deformed to pressurize the agent, thereby forcing it out through the lumens of the microneedles 120.

A 500 μm tall prototype microneedle 120 fabricated using the method depicted in FIGS. 1A-1G was used to inject fluorescent beads into pigskin. The microneedle 120 was bound to the tip of a conventional 1 ml syringe. The syringe was filled with a 0.01 wt % suspension of 2.28 μm fluorescent beads in water. The microneedle 120 was pressed against the skin, and a force of approximately 2 N was applied to the syringe plunger for 5 minutes. The skin surface near the injection site was washed with water and dried with a wipe. A Nikon® Eclipse® C1 confocal microscope (Melville, N.Y.) was used to scan the distribution of the fluorescent beads inside the skin. The confocal scan of the injection site indicated delivery of the fluorescent beads to a depth of 250 μm into the skin. A control test was performed by applying a fluorescent bead solution to the surface of pigskin for 10 minutes, washing the skin, and then taking a confocal scan of the skin. The control test did not show any fluorescent microspheres below the skin surface. This suggests that pigskin is not permeable to the fluorescent beads and that the prototype microneedle 120 may be useful for transdermal delivery of drugs, including suspensions.

A 500 μm tall prototype nickel microneedle 120 fabricated using the method depicted in FIGS. 1A-1G was used to inject a fluorescent chemotherapeutic drug (doxorubicin) into pigskin. A backing plate of the microneedle was bonded to a drug container that was connected to a conventional syringe via a flexible plastic capillary tube. The syringe was filled with a 174 μM solution of doxorubicin in water. The syringe was placed in a commercial syringe pump system (from KD Scientific™ of Holliston, Mass.). The microneedle 120 was applied to a shaved pigskin sample. The pump was set to push the plunger to generate a constant flow rate of 0.2 μL/minute for 3 minutes. This flow rate was selected based on a study investigating the efficiency of transdermal drug injection using silicon microneedles (U. O. Häfeli, et al., (2009), Biomed. Microdevices, Vol. 11, pp. 943-950) which found an average delivery rate of 0.2 μL/minute through each needle in an injection trial. After the injection, the skin was cleaned and then scanned using confocal microscopy. The confocal scans showed penetration of the doxorubicin down to a depth of approximately 130 μm.

In some embodiments, an agent is embedded within the structure of a microneedle 120 and/or coated on the surface of a microneedle 120, and insertion of the microneedle 120 into the skin causes the agent to be transferred to the skin. The microneedle 120 may be a solid or hollow microneedle 120. The microneedle 120 may not need to be removed from the mold pillar with which it was formed.

Application 2: Perforation Devices

Microneedles 120 may be used as perforation devices for perforating (e.g. creating holes, scratches, scars, etc.) in skin (e.g. the stratum corneum). Solid or hollow microneedles 120 may be used. The microneedles 120 may be applied to skin by any suitable method including stamping and rolling (e.g. attaching an array of microneedles 120 to a roller and rolling the roller across an area of skin).

An agent may be applied to an area of skin before and/or after the area of skin is perforated. The perforations in the skin may increase the permeability of the skin and may enhance the uptake of the agent through the skin.

Vacuum suction devices may be used to extract biological fluids (e.g. interstitial fluid and blood) from perforated skin.

Application 3: Sensing

Microneedles 120 may be used to take up one or more agents. For example, an array of hollow microneedles 120 may be used to penetrate skin and take up a bodily fluid (e.g. an interstitial fluid containing an anti-cancer drug). The fluid may be actively drawn into the microneedles 120 by any suitable method including pressure, electric fields, capillary forces, and diffusion through a carrier liquid within the microneedles 120. The fluid may then be directed to one or more sensing regions. The fluid may be transported to the sensing regions via channels. The sensing regions may be located on the side of the microneedle array opposite from the side that the fluid enters the microneedle array. The sensing regions may comprise any suitable sensors, including optical and electrochemical sensors.

Application 4: Material Deposition

Microneedles 129 may be used to deposit material (e.g. fluids, powders, etc.). Microneedles 120 may act as nozzles. Droplets of fluid may be ejected from individual microneedle openings (in a manner similar to inkjet printing). Alternatively, jets of fluid may be ejected from individual microneedle openings. In the case of a relatively viscous fluid, the ejection may form a relatively viscous jet. Material may be ejected using any suitable method including the application of pressure and electric fields.

Material may be ejected from an array of microneedles 120. Material may be ejected from all the microneedles 120 of the array simultaneously. The microneedles 120 may be actuated individually to control the ejection of material from each individual microneedle 120. The microneedles 120 may be actuated in groups to control the ejection of material from each group of microneedles 120. The material ejected from each microneedle 120 may be the same or different as the material ejected from other microneedles 120. The material ejected from each microneedle 120 may be changed over time. The material ejected from the microneedles 120 may be deposited onto a substrate and may form a patterned structure.

Application 5: Electrodeposition

Microneedles 120 may be used to deposit material through electrospinning or electro spray deposition. An electric field may be applied between a material to be ejected and a target substrate (or an electrode beneath the target substrate). The material may be contacted by an electrode before it exits a microneedle 120, or the microneedle 120 may be used as an electrode. The material may also be driven by a positive displacement pump. The material may break up into droplets as it exits the microneedle 120, or it may form a jet. The electric field may cause the jet to undergo a whipping motion, stretching the jet. If the material is a polymer solution, the solvent may evaporate and leave behind a very thin fiber.

Application 6: Combustion

A microneedle 120 may be used as a fuel injector for liquid or gas fuel. The fuel may be ejected through the microneedle 120. The fuel may comprise a mixture of materials that can react with each other. The fuel may react with the surrounding air or with a substance exiting other microneedles 120. The fuel may be ignited.

Application 7: Tattoos

Microneedles 120 may be used to create tattoos. Relatively short microneedles 120 may be used to create temporary tattoos. Relatively long microneedles 120 may be used to create permanent tattoos.

Application 8: Imaging

Microneedles 120 may be embedded into a material or tissue and imaged. For example, a microneedle array may form part of a medical device such as an instrument or an implant, and this device may be inserted or implanted into tissue. The microneedle array may be imaged by any suitable imaging process including radiological imaging, x-ray imaging, computed tomography imaging, fluoroscopy/angiography imaging, and any combination thereof. Metal microneedles 120 may have good x-ray contrast properties.

While a number of exemplary aspects and embodiments have been discussed above, those of skill in the art will recognize certain modifications, permutations, additions and sub-combinations thereof. It is therefore intended that the following appended claims and claims hereafter introduced are interpreted to include all such modifications, permutations, additions and sub-combinations as are within their true spirit and scope.

What is claimed is:

1. A method for fabricating a microneedle, the method comprising:
   providing a mold pillar;
   forming an electrically-conductive polymer layer over the mold pillar;
   depositing a metal layer over the electrically-conductive polymer layer to provide a microneedle;
   wherein depositing the metal layer over the electrically-conductive polymer layer comprises: electroplating the metal layer onto the electrically-conductive polymer layer and using the electrically-conductive polymer layer as an electrode in the electroplating process.

2. The method of claim 1 wherein the mold pillar extends away from a surface of a substrate.

3. The method of claim 1 wherein the mold pillar comprises a cone-shaped mold pillar with a base and a tip and wherein providing the mold pillar comprises using an etching process to sharpen the tip of the mold pillar.

4. The method of claim 1 wherein the mold pillar comprises a protective layer for protecting the mold pillar from subsequent processes and enabling use of the mold pillar for fabricating a plurality of microneedles.

5. The method of claim 1 wherein forming the electrically-conductive polymer layer over the mold pillar comprises using a solvent-casting process.

6. The method of claim 5 wherein solvent-casting the electrically-conductive polymer layer comprises adding a polymer and conductive particles to a solvent.

7. The method of claim 6 comprising adding a surfactant to the solvent.

8. The method of claim 1 wherein the electrically-conductive polymer layer comprises an apertured electrically-conductive polymer layer.

9. A method according to claim 8 comprising forming the apertured electrically-conductive polymer layer by coating the mold pillar with the electrically-conductive polymer layer and then removing a portion of the electrically-conductive polymer layer to form an aperture.

10. The method of claim 9 comprising removing the portion of the electrically-conductive polymer layer by one or more of dry etching, photolithography, mechanical grinding, and localized heating.

11. The method of claim 1 wherein the metal layer comprises a first sub-layer of metal adjacent the electrically-conductive polymer layer and second sub-layer of metal adjacent the first layer of metal.

12. The method of claim 11 wherein:
   the first sub-layer of metal comprises a structural metal and the second sub-layer of metal comprises a biocompatible metal; or
   the first metal sub-layer comprises a biocompatible metal and the second metal sub-layer comprises a structural metal.

13. The method of claim 1 further comprising applying a coating to the microneedle.

14. The method of claim 13 comprising:
   removing the microneedle from the mold pillar; and
   applying the coating to an interior surface of the microneedle, the interior surface of the microneedle masked by the mold pillar prior to removal of the microneedle from the mold pillar.

15. The method of claim 13 wherein the coating comprises at least one of a biocompatible coating, an electrically-insulating coating, and a metal.

16. The method of claim 1 comprising removing the microneedle from the mold pillar and re-using the mold pillar to fabricate a second microneedle.

17. A method for fabricating a microneedle, the method comprising:
   providing a mold pillar;
   forming an electrically-conductive polymer layer over the mold pillar wherein the electrically-conductive polymer layer comprises an apertured electrically-conductive polymer layer;
   depositing a metal layer over the electrically-conductive polymer layer to provide a microneedle; and
   forming the apertured electrically-conductive polymer layer by:
      applying a coating to a region of the mold pillar; and
      solvent-casting the electrically-conductive polymer layer onto the mold pillar using a solvent that is repelled by the coating so that the electrically-conductive polymer layer is created with an aperture located at the coated region.

18. A method for fabricating a microneedle, the method comprising:
   providing a mold pillar;
   forming an electrically-conductive polymer layer over the mold pillar wherein the electrically-conductive polymer layer comprises an apertured electrically-conductive polymer layer;
   depositing a metal layer over the electrically-conductive polymer layer to provide a microneedle; and
   forming the apertured electrically-conductive polymer layer by:
      orienting the mold pillar so that a first region of the mold pillar is vertically higher than a second region of the mold pillar; and
      solvent-casting the electrically-conductive polymer layer onto the mold pillar so that the force of gravity causes the electrically-conductive polymer layer to form with an aperture at the first region.

19. The method of claim 17 wherein depositing the metal layer over the electrically-conductive polymer layer comprises electroplating the metal layer onto the electrically-conductive polymer layer and using the electrically-conductive polymer layer as an electrode in the electroplating process.

20. The method of claim 17 wherein depositing the metal layer over the electrically-conductive polymer layer comprises sputtering the metal layer onto the electrically-conductive polymer layer.

21. A method for fabricating a first microneedle and a second microneedle, the method comprising:
   providing a mold pillar;
   depositing a first metal layer over the mold pillar to provide a first microneedle;
   removing the first microneedle from the mold pillar;
   depositing a second metal layer over the mold pillar to provide a second microneedle;
   wherein depositing the first metal layer over the mold pillar to provide the first microneedle comprises:
      forming an electrically-conductive polymer layer over the mold pillar; and
      depositing the first metal layer over the electrically-conductive polymer layer;
      wherein depositing the first metal layer over the electrically-conductive polymer layer comprises: electroplating the first metal layer onto the electrically-conductive polymer layer and using the electrically-conductive polymer layer as an electrode in the electroplating process.

22. A method for fabricating an apertured microneedle, the method comprising:
providing a mold pillar;
forming an apertured electrically-conductive layer over the mold pillar;
depositing a metal layer over the apertured electrically-conductive layer to provide an apertured microneedle;
wherein forming the apertured electrically-conductive layer over the mold pillar comprises using a solvent-casting process;
wherein the apertured electrically-conductive layer comprises an apertured electrically conductive polymer layer; and
wherein depositing the metal layer over the apertured electrically-conductive layer comprises: electroplating the metal layer onto the apertured electrically-conductive polymer layer and using the apertured electrically-conductive polymer layer as an electrode in the electroplating process.

* * * * *